US00PP22950P2

(12) United States Plant Patent
Zaiger et al.

(10) Patent No.: US PP22,950 P2
(45) Date of Patent: Aug. 14, 2012

(54) CHERRY TREE NAMED 'ROYAL BRYNN'

(50) Latin Name: *Prunus avium*
Varietal Denomination: Royal Brynn

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 13/065,887

(22) Filed: Apr. 1, 2011

(51) Int. Cl.
*A01H 5/00* (2006.01)

(52) U.S. Cl. ..... Plt./181

(58) Field of Classification Search ..... Plt./181
See application file for complete search history.

*Primary Examiner* — Annette Para

(57) ABSTRACT

A new and distinct variety of cherry tree. The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright growth of tree.
2. Heavy and regular production of large size fruit.
3. Fruit with good handling and shipping quality.
4. Fruit with an attractive red skin color.
5. Fruit with very good flavor.

1 Drawing Sheet

Botanical classification: *Prunus avium.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of cherry tree was originated and asexually reproduced by us in our experimental orchard located near Modesto, Stanislaus County, Calif.

PRIOR VARIETIES

Among the existing varieties of cherry trees, which are known to us, and mentioned herein, 'Royal Edie' Cherry (U.S. Plant Pat. No. 19,365) and the proprietary cherry selection '23ZD1031'.

STATEMENT REGARDING FEDERALLY SPONSORED RESEARCH AND DEVELOPMENT

Not applicable.

ORIGIN OF THE VARIETY

The present new variety of cherry tree (*Prunus avium*) was developed by us in our experimental orchard located near Modesto, Calif. The new cherry tree originated from an open pollinated proprietary seedling selection with the field identification '23ZD1031'. The seed parent (23ZD1031) originated from an open pollinated 'Royal Edie' Cherry (U.S. Plant Pat. No. 19,365). A large number of these open pollinated seedlings were budded on established trees of 'Mahaleb' Rootstock (non-patented) to accelerate fruit production. Under close and careful observation the present seedling exhibited desirable fruit and tree characteristics and was selected in 2006 for asexual propagations and commercialization.

ASEXUAL REPRODUCTION OF THE VARIETY

Asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of cherry tree is of large size, vigorous upright growth and a regular and productive bearer of large size fruit that has an attractive red skin color. The fruit is further characterized by its firm flesh, good handling and shipping quality and very good flavor. In comparison to its immediate seed parent (23ZD1031) the fruit is larger in size with firmer flesh, more desirable fruit quality and is approximately 3 days later in maturity. In comparison to its ancestor 'Royal Edie' Cherry (U.S. Plant Pat. No. 19,365) the fruit of the new variety is approximately 12 days earlier in maturity.

PHOTOGRAPH OF THE VARIETY

The accompanying color photographic illustration shows typical specimens of the foliage and fruit of the present new cherry variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 8 year old tree and the colors are as nearly true as is reasonably possible in a color representation of this type.

DESCRIPTION OF THE VARIETY

The following is a detailed botanical description of the new variety of cherry tree, its flowers, foliage and fruit, as based on observations of 8 year old specimens grown near Modesto, Calif., with color in accordance with Munsell Book of Color.

Tree:

*Size*.—Large. Tree pruned to 3 to 4 meters in height and width for economical harvesting of fruit. Varies with different cultural practices.

*Vigor*.—Vigorous. Tree growth reaching 1 to 2 meters the first growing season. Growth rate varies with soil type and depth, cultural practices and climatic conditions.

*Form*.—Upright, usually pruned to vase shape.

*Branching habit*.—Upright, crotch angle approximately 35°, the weight of the fruit tends to increase branch angles.

*Productivity*.—Productive, produces adequate fruit set annually.

*Bearer*.—Regular, adequate fruit set 5 consecutive years.

*Fertility*.—Self-sterile, pollinator required.

*Density*.—Medium dense. Normally pruned to vase shape to allow sunlight into center of tree to enhance health of fruit spurs.

*Hardiness*.—Hardy in all stone fruit growing areas of California. Tree grown in USDA Hardiness Zone 9. Winter chilling requirement is approximately 750 hours at or below 45° F.

Trunk:

*Size*.—Large. Measured 30.5 cm at 45.7 cm above ground on an 8 year old tree. Varies with soil type, climatic conditions and cultural practices.

*Stocky*.—Medium stocky.

*Texture*.—Medium rough, roughness increases with age.

*Color*.—Varies from 7.5YR 6/2 to 7.5YR 3/2.

Branches:

*Size*.—Medium. Average circumference 12.7 cm at 1.2 meters above ground.

*Surface texture*.—New growth relatively smooth. Older growth medium rough, roughness increases with age.

*Lenticels*.—Average number 28 in a 25.8 square cm section. Average length 4.5 mm. Average width 1.1 mm. Color varies from 7.5YR 6/10 to 10YR 6/10.

*Color*.—New growth varies from 2.5GY 6/8 to 5GY 5/8. Old growth varies from 7.5YR 2/4 to 10YR 3/2, varies with age of growth.

Leaves:

*Size*.—Large. Average length 169.9 mm. Average width 77.9 mm.

*Form*.—Lanceolate.

*Apex*.—Acuminate.

*Base*.—Cuneate.

*Margin*.—Doubly serrate.

*Thickness*.—Medium.

*Surface texture*.—Upper surface relatively smooth, slight indentation over leaf veins, glabrous. Lower surface relatively smooth, slight ridges created by midrib and pinnate venation, glabrous.

*Petiole*.—Average length 37.7 mm. Average width 2.2 mm. Longitudinally grooved. Color varies from 2.5GY 5/8 to 7.5R 2/4 where exposed to the sun. Surface glabrous.

*Glands*.—Shape — reniform. Average length 2.2 mm. Average width 1.5 mm. Number varies from 2 to 4, average number 2. Located primarily on the upper portion of the petiole. Color varies from 7.5R 3/6 to 7.5R 3/8.

*Stipules*.—Average length 11.6 mm. Margin — serrate. Color varies from 2.5GY 6/6 to 5R 4/8.

*Color*.—Upper surface varies from 5GY 3/6 to 7.5GY 3/6. Lower surface varies from 5GY 4/4 to 7.5GY 4/4. Midvein color varies from 2.5GY 6/6 to 5GY 7/6.

Flower buds:

*Size*.—Large. Average. length 16.9 mm. Average diameter 9.1 mm.

*Hardiness*.—Hardy, with respect to California winters.

*Form*.—Conical, becoming elongated just before opening.

*Pedicel*.—Average length 13.5 mm. Average width 1.4 mm. Color varies from 5GY 6/6 to 5GY 5/6.

*Color*.—N 9.5/(white).

*Number of buds per spur*.—Average number 7, varies from 5 to 9.

Flowers:

*Blooming period*.—Date of First Bloom Mar. 15, 2010. Date of Petal Fall Mar. 24, 2010, varies slightly with climatic conditions.

*Size*.—Large. Average height 18.1 mm. Average diameter 32.0 mm.

*Petals*.—Size — large. Number — normally 5, alternately arranged to sepals. Average length 17.7 mm. Average width 15.7 mm. Form — orbicular. Margin — sinuate. Color — N 9.5/(white). Both surfaces glabrous.

*Sepals*.—Size — large. Number — normally 5, alternately arranged to petals. Average length 6.9 mm. Average width 4.9 mm. Form — triangular. Margin — entire. Color — upper surface varies from 5GY 5/6 to 7.5GY 5/6. Lower surface varies from 5GY 5/6 with 5R 3/6. Both upper and lower surfaces glabrous.

*Stamens*.—Average number per flower 38, varies from 35 to 41. Average filament length 12.2 mm. Filament color N 9.5/(white). Anther color varies from 5Y 8/10 to 5Y 7/10.

*Pollen*.—Self sterile, pollinator required. Color varies from 2.5Y 7/12 to 5Y 7/12.

*Pistil*.—Normally one per flower. Average length 16.3 mm. Stigma height approximately 1.0 mm above anthers. Color varies from 10Y 7/6 to 2.5GY 7/6. Surface — glabrous.

*Fragrance*.—Heavy aroma.

*Color*.—N 9.5/(white).

*Number flowers per flower bud*.—Average 5, varies from 1 to 5.

*Pedicel*.—Average length 16.1 mm. Average width 1.5 mm. Color varies from 5GY 5/6 to 2.5GY 7/6.

Fruit:

*Maturity when described*.—Firm ripe.

*Date of first picking*.—May 23, 2010.

*Date of last picking*.—May 31, 2010, varies slightly with climatic conditions.

*Size*.—Large. Average diameter axially 24.7 mm. Average transversely in suture plane 27.8 mm. Average weight 14.2 grams, varies slightly with fertility of the soil, amount of thinning and climatic conditions.

*Form*.—Globose. Slightly flattened at base and apex.

*Suture*.—Nearly smooth, extends from base to apex.

*Ventral surface*.—Nearly smooth to very slightly lipped.

*Apex*.—Slightly retuse.

*Base*.—Slightly retuse.

*Stem cavity*.—Rounded. Average depth 1.8 mm. Average diameter 4.1 mm.

Stem:

*Size*.—Medium. Average length 38.8 mm. Average diameter 1.5 mm.

*Color*.—Varies from 5GY 5/6 to 5GY 4/6.

Flesh:

*Ripens*.—Evenly.

*Texture*.—Firm.

*Fibers*.—Few, small, tender.

*Firmness*.—Firm, comparable to most commercial varieties.

*Aroma*.—Moderate.

*Amydgalin*.—Undetected.

*Eating quality*.—Very good.

*Flavor*.—Very good, good balance between acid and sugar.

*Juice*.—Moderate amount, enhances flavor.

*Brix*.—Average Brix 18.9°, varies slightly with amount of fruit per tree and climatic conditions.

*Color*.—Varies from 5R 3/8 to 7.5R 2/8. Pit cavity color varies from 5R 2/4 to 7.5R 2/6.

Skin:

*Thickness*.—Medium.

*Surface*.—Smooth.

*Bloom*.—Wanting.

*Tendency to crack*.—None during dry weather. Only slight tendency to crack in wet weather, varies with stage of maturity.

*Color*.—Varies from 5R 2/6 to 7.5R 2/8.

*Tenacity*.—Tenacious to flesh.

*Astringency*.—None.

Stone:

*Type*.—Clingstone.

*Size*.—Medium. Average length 9.6 mm. Average width 9.3 mm. Average thickness 7.8 mm.

*Form*.—Nearly globose.

*Base*.—Flat.

*Apex*.—Rounded.

*Surface*.—Nearly smooth except for small ridges near the suture.

*Sides*.—Equal to unequal. Some stones have one side extending further from the suture plane.

*Ridges*.—A small, narrow ridge on each side of suture, extends from base to apex.

*Tendency to split*.—None.

*Color*.—Varies from 7.5YR 6/6 to 7.5YR 5/6 when dry.

Kernel:

*Size*.—Medium. Average length 7.5 mm. Average width 6.1 mm. Average depth 5.4 mm.

*Form*.—Ovate.

*Viability*.—Viable, good embryo development.

*Skin*.—Color varies from 2.5Y 8.5/4 to 5Y 9/4.

Use:

*Dessert*.—Market — local and long distance.

Keeping quality: Good, held well for 3 weeks in cold storage at 38° to 42° F. and maintained good appearance and eating quality.

Shipping quality: Good, showed minimal bruising or scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of cherry tree, substantially as illustrated and described.

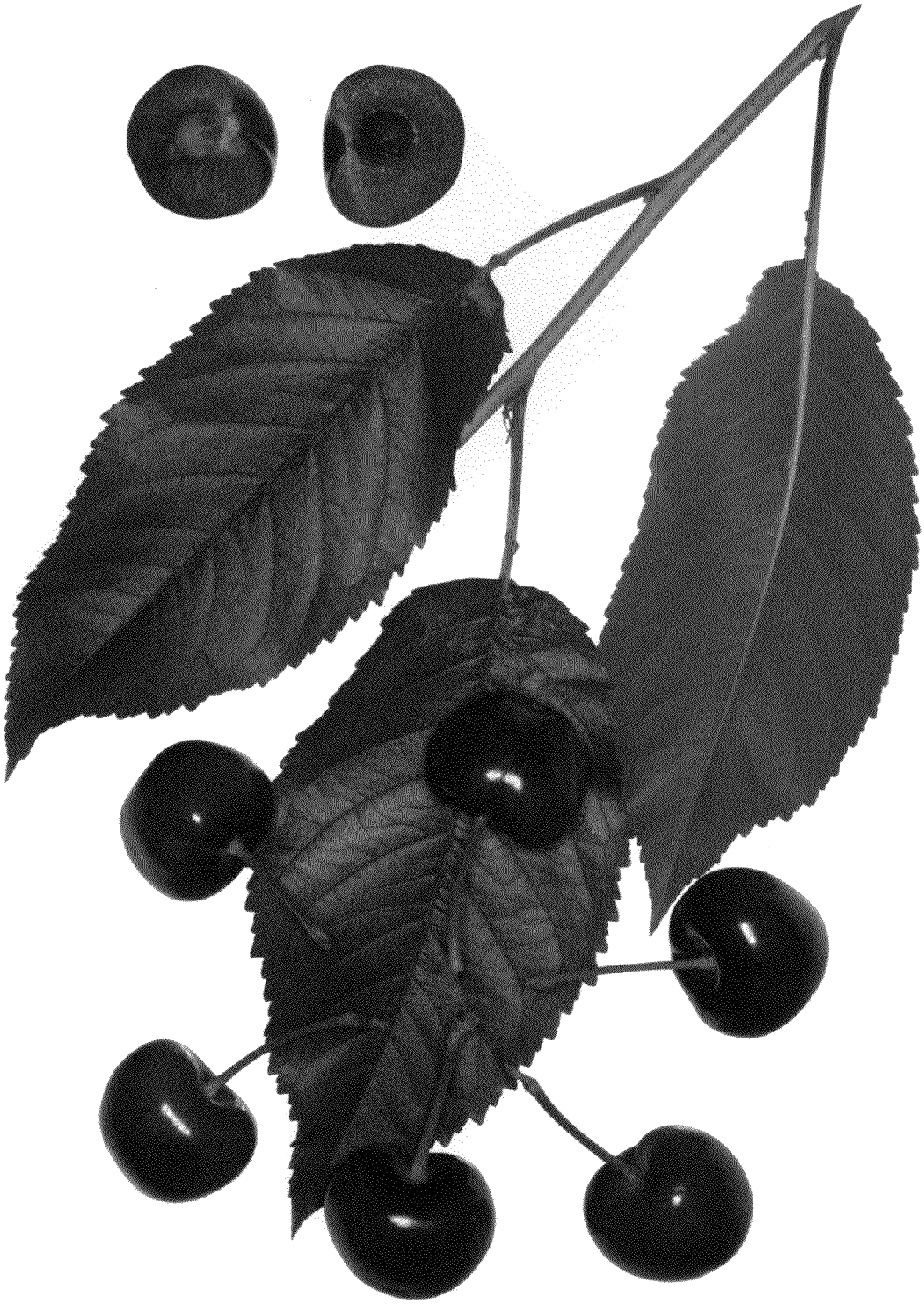

* * * * *